United States Patent [19]

Caswell et al.

[11] Patent Number: 4,695,395

[45] Date of Patent: Sep. 22, 1987

[54] CLEANING COMPOSITIONS WITH SKIN PROTECTION AGENTS

[75] Inventors: Michael L. Caswell, Memphis, Tenn.; James J. Corr, Huntington, N.Y.; Mark S. Dobrovolny, Edison, N.J.; Lynn H. Lander, Harrington Park, N.J.; William R. Narath, Parsippany, N.J.; Richard F. Theiler, Harrington Park, N.J.

[73] Assignee: Lever Brothers Company, New York, N.Y.

[21] Appl. No.: 886,575

[22] Filed: Jul. 16, 1986

Related U.S. Application Data

[63] Continuation-in-part of Ser. No. 654,291, Sep. 25, 1984, abandoned.

[51] Int. Cl.$^4$ .......................... C11D 9/32; C11D 17/00
[52] U.S. Cl. ..................................... 252/121; 252/108; 252/132; 252/DIG. 16
[58] Field of Search ....... 252/108, 121, 132, DIG. 16, 252/117

[56] References Cited

U.S. PATENT DOCUMENTS

| | | | |
|---|---|---|---|
| 2,894,912 | 7/1959 | Geitz | 252/121 |
| 3,043,779 | 7/1962 | Parke et al. | 252/117 |
| 3,376,229 | 4/1968 | Haass | 252/117 |
| 3,607,766 | 9/1971 | Woo et al. | 252/121 |
| 3,879,309 | 4/1975 | Gatti et al. | 252/117 |
| 4,007,125 | 2/1977 | Prince | 252/117 |
| 4,180,470 | 12/1979 | Tokosh et al. | 252/121 |
| 4,260,507 | 4/1981 | Barrett | 252/121 |

FOREIGN PATENT DOCUMENTS

| | | |
|---|---|---|
| 2402223 | 7/1974 | Fed. Rep. of Germany . |
| 1548302 | 10/1968 | France . |
| 1580491 | 9/1969 | France . |
| 55496 | 2/1968 | Luxembourg . |
| 479695 | 11/1969 | Switzerland . |
| 1001962 | 8/1965 | United Kingdom . |
| 1130705 | 10/1968 | United Kingdom . |
| 1165611 | 10/1969 | United Kingdom . |
| 1178688 | 1/1970 | United Kingdom . |
| 1238865 | 7/1971 | United Kingdom . |
| 1240005 | 7/1971 | United Kingdom . |
| 1460442 | 1/1977 | United Kingdom . |

OTHER PUBLICATIONS

"The Soap Chamber Test", by Frosch & Kligman, J. Amer. Acad. Derm., pp. 35–41 (1979).
"Quality Parameters for Sodium Cocoyl Isethionate", by Login, Happi, pp. 56–60 and 88, Sep. 1984.

*Primary Examiner*—Prince E. Willis
*Attorney, Agent, or Firm*—Milton L. Honig; James J. Farrell

[57] ABSTRACT

Isethionate salts have been discovered to provide protection for the skin against damage from contact with soap or other surfactants. A mild to the skin cleaning composition is provided comprising fatty acid soap in amounts greater than 25% and an isethionate salt such as sodium isethionate, the ratio of soap to isethionate ranging from 1:2 to abut 200:1. Sodium $C_8$–$C_{18}$ acyl isethionate may be incorporated as a further component into the cleaning composition, although in an amount not to exceed that of the soap.

7 Claims, No Drawings

CLEANING COMPOSITIONS WITH SKIN PROTECTION AGENTS

CROSS REFERENCE

This application is a continuation-in-part of Ser. No. 654,291, filed Sept. 25, 1984, now abandoned.

BACKGROUND OF THE INVENTION

1. Field of the Invention

The invention relates to cleaning compositions containing a major amount of soap and a mildness improving component to protect skin against surfactant damage.

2. The Prior Art

Soap is mankind's oldest surfactant. Although soap is efficient at cleaning, it requires formulation to overcome many physical property defects. Additives have been discovered which improve soap's lather, fragrance, visual appeal and other aesthetic properties.

More recently, attention has been drawn to the harshness problem of soap toward skin. Eighteen well-known toilet soaps were evaluated by Frosch & Kligman, "J. Amer. Acad. Derm.", pp. 35 (1979). Great differences were noted in their effect upon skin. Most had an appreciable irritancy. The study revealed that substantial replacement of soap with an alternative detergent such as acyl fatty isethionate would provide a more skin compatible system. Unfortunately, this alternative is expensive. Cheaper solutions to the harshness problem would be desirable.

Reports of blending soap with acyl fatty isethionates, presumably to lower costs, have been numerous. U.S. Pat. No. 2,894,912 (Geitz) extols the virtues of toilet bars containing from 30 to 70% acyl fatty isethionate and 2.5 to 25% soap. In U.S. Pat. No. 4,260,507 (Barrett), a composition with major amounts of soap, 60–97%, was combined with minor amounts, 3–40%, acyl fatty isethionate. These toilet bars were claimed to have exceptional lathering properties.

Acyl fatty isethionate is prepared by direct esterification of $C_{12}$–$C_{25}$ fatty acid with the alkali metal salt of isethionic acid (known also as hydroxyethane sulfonic acid). Unesterified alkali metal isethionate itself has been reported as a toilet bar processing aid in U.S. Pat. No. 4,180,470 (Tokosh et al). Alkali metal isethionates, however, have never been reported as mildness improvers nor their use suggested in formulations where soap is present in greater amount than 25 wt. % of the total composition.

It is an object of this invention to provide a low cost cleaning composition containing major amounts of soap but substantially milder to skin than pure soap.

Another object of this invention is to provide a method for protecting skin against damage from contact with soap or any other surfactant.

SUMMARY OF THE INVENTION

A cleaning composition is provided comprising:

(a) a fatty acid soap in an amount greater than 25%; and (b) a mildness improving salt of following structure:

HO—CHRCH$_2$—SO$_3$M where

R is hydrogen or a $C_1$–$C_7$ alkyl or alkenyl radical;

M is a cation selected from either alkali metal, alkaline earth metal, ammonium, alkyl ammonium and mono-, di- or trialkanolammonium ions; wherein the ratio of soap to mildness improving salt ranges from about 1:2 to about 200:1; and (c) from 1% to 15% $C_8$–$C_{22}$ free fatty acid.

DETAILED DESCRIPTION OF THE INVENTION

According to the present invention, it has been found that non-acylated isethionate salts when incorporated into soap formulations prevent skin damage, a problem normally associated with unmodified soap. Unlike acyl fatty isethionates, their non-acylated progenators impart skin mildness at a concentration level significantly below that achieved through the acylated esters.

The term "soap" is used herein in its popular sense, i.e., the alkali metal or alkanol ammonium salts of aliphatic alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. The soaps useful herein are the well known alkali metal salts of natural or synthetic alphatic (alkanoic or alkenoic) acids having about 12 to 22 carbon atoms, preferably about 12 to about 18 carbon atoms. They may be described as alkali metal carboxylates of acyclic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12–18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. The soap may be prepared from coconut oil, in which case the fatty acid content is about 85% of $C_{12}$–$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Total soap content of the instant compositions must be greater than 25 wt. %. Usually, from about 30% to 98% of the composition is soap. Preferably, the concentration of this component ranges from about 40% to 70%, more preferably 50% to 65%.

Soap formulations encompassed by this invention may either be in liquid or toilet bar form.

Skin mildness improvers hereby disclosed are salts of isethionate. Effective salt cations may be selected from the group consisting of alkali metal, alkaline earth metal, ammonium, alkyl ammonium and mono-, di- or tri-alkanolammonium ions. Specifically preferred cations include sodium, potassium, lithium, calcium, magnesium, ammonium, triethylammonium, monoethanolammonium, diethanolammonium or triethanolammonium ions.

Particularly preferred as a mildness improver is simple, unsubstituted sodium isethionate of the general formula wherein R is hydrogen.

The skin mildness improver will be present from about 0.5% to about 50%. Preferably, the mildness improver is present from about 1% to about 25%, more preferably from about 2% to about 15%, optimally from 5% to 10%, by weight of the total composition.

Detergents other than soap may also be present in the formulations of this invention. Their presence will, however, be no greater than the amount of soap present. Adjunct detergents may be chosen from the alkali metal, magnesium or ammonium salts selected from the group consisting of:

$C_{12}$–$C_{16}$ hydroxyalkane sulfonates,
$C_8$–$C_{18}$ acyl isethionates,
$C_8$–$C_{18}$ N-acyl taurinates,
$C_{12}$–$C_{18}$ alkyl sulfates,
$C_{12}$–$C_{18}$ alkyl ether sulfates,
$C_{12}$–$C_{16}$ alkyl phosphonates and phosphates,
$C_{12}$–$C_{16}$ mono-alkyl succinates and maleates,
$C_6$–$C_{14}$ dialkylsulfosuccinates,
$C_{16}$–$C_{20}$ alkane disulfonates, and
$C_8$–$C_{18}$ alkene sulfonates.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 40% by weight of the total composition. Preferably, this component is present from about 15% to about 30%.

Free fatty acids of 8–22 carbon atoms are desirably incorporated within the compositions of the present invention. Some of these fatty acids are present to operate as superfatting agents and others as skin feel and creaminess enhancers. Superfatting agents enhance lathering properties and may be selected from fatty acids of carbon atoms numbering 8–18, preferably 10–16, in an amount up to 25% by weight of the composition. Skin feel and creaminess enhancers, the most important of which is stearic acid, are also desirably present in these compositions. Levels lower than 25% of stearic acid are, however, necessary in certain formulations where it is desired to accentuate the performance of the mildness improving salt disclosed by the present invention. Thus, stearic acid levels in these formulations must be held between 4 and 10%, preferably between 5 and 9%, but most preferably between 6 and 8%.

Other performance chemicals and adjuncts may be needed with these compositions. The amount of these chemicals and adjuncts may range from about 1% to about 40% by weight of the total composition. For instance, from 2 to 10% of a suds-boosting detergent salt may be incorporated. Illustrative of this type additive are salts selected from the group consisting of alkali metal and organic amine higher aliphatic fatty alcohol sulfates, alkyl aryl sulfonates, and the higher aliphatic fatty acid taurinates.

Adjunct materials including germicides, perfumes, colorants, pigments such as titanium dioxide and water may also be present.

SKIN MILDNESS TESTS

Frosch-Kligman Soap Chamber Test

The Frosch-Kligman Soap Chamber Test is designed to evaluate the mildness of surfactant compositions on individuals with hypersensitive skin. An individual is deemed hypersensitive if, after occlusion with a 0.75% sodium lauryl sulfate patch for six hours, the treated site appears confluently red twenty-four hours after the patch is applied. Approximately 30% of those screened for this study were found to have hypersensitive skin. Twenty-nine hyper-reactive qualified panelists participated in the experiments of Example 1.

Hill Top Chambers TM (25 mm diameter) were affixed to Dermicel TM -Hypoallergenic cloth tape (Johnson & Johnson) to create an occluded patch. A Gilson TM micropipette was used to deliver 0.20 mL of solution to each of the respective chambers. Each of the panelists was assigned one of 31 randomized patched sequences.

Following removal of the patch on Day 5, each patched site was assessed by three trained judges 3 hours after patch removal. Three categories were evaluated according to the following (assessment) scales:

| Erythema | Scaling | Fissuring |
| --- | --- | --- |
| 0 = no erythema | 0 = no scaling | 0 = no fissuring |
| 1 = slight redness, diffuse | 1 = fine | 1 = fine cracks |
| 2 = moderate, uniform | 2 = moderate | 2 = single or multiple broad fissures |
| 3 = intense redness | 3 = severe with large flakes | 3 = wide cracks with hemmorage or exudation |

A preference rating for each site was also made. Panelists were assessed again on Day 8. These data were statistically analyzed using a non-parametric Friedman's Test and Nemenyi's Procedure.

Guinea Pig Immersion Tests

The Guinea Pig Immersion Test has also been used as a predictive model for assessing skin irritation resulting from detergent insult.

Adult male albino Hartley guinea pigs served as the animal panelists. They were fed standard guinea pig chow and tap water ad libitum except during treatment periods. Prior to testing, the animals were observed for signs of skin defects and general disease. The animals were then acclimated in the facility for five days before start of immersion treatments. During the treatment period, skin temperature and animal weight was monitored. An evaporimeter was used to measure transepidermal water loss. Skin thickness and surface pH were also measured. Laboratory conditions were maintained at 72°±2° F. and approximately 50% room humidity. Lighting was synchronized to 12 hours light followed by 12 hours darkness. Body weights were taken daily. Each animal was observed daily for sickness, and assessed for skin abnormalities. On the first and each subsequent day of experimentation, the abdominal surface of the guinea pig was closely clipped. Following assessments, the guinea pig was placed in a perforated canister with a "lock on" lid. The caged guinea pig was then placed in a 2-liter clear plastic Nalgene beaker containing circa 1.4 liters of pre-heated (38°–40° C.) immersion solution. This volume allowed immersion up to the thoracic axilla of each animal. Guinea pigs were immersed for 30 minutes with the immersion tank water held at 40° C. Immediately thereafter, each animal was removed from the immersion beaker, transferred to a 10 liter bucket of distilled water (40° C.) and vigorously rinsed. The animal was then removed from its container, partially dried with paper towels and placed for thirty minutes in an infrared heated (90° F.) incubator. After completion of the heated incubation period, the animal was returned to its cage. Three hours after initiating the first immersion, a second identical immersion procedure was executed. Tests continued for a period of 10–12 days.

After each immersion, the skin was rated for erythema, flaking and roughness response. Relative response scores ratings are outlined below:

| Erythema | Flaking | Roughness |
| --- | --- | --- |
| 0-No Effect | 0-No Response | 0-Smooth, normal response |
| 1-Slight | 1-Slight response | 1-Slight response |
| 2-Moderate | 2-Moderate scaling | 2-Moderate response |
| 3-Severe | 3-Moderate scaling with some sloughing of epidermis | 3-Definite response |
| 4-Severe with hemorrhage | 4-Severe scaling, sloughing of epidermis, marked cracking | 4-Definite roughness with cracking |
| 5-Necrosis | 5-Sloughing of large areas of epidermis, deep cracking with possible hemorrhage | 5-Severe roughness with deep cracking and oozing |

Within each category of skin damage, responses were averaged for the full 10–12 day period. Examples in this specification record the relative response scores averaged from the average of each animal.

Flex Wash Test

The Flex Wash procedure consists of three daily 60 second washes of the antecubital fossa (flex area of elbow). This method is designed to produce erythema quickly. Erythemal response varies only slightly with temperature and humidity fluctuations, unlike the Frosch-Kligman Test, making the protocol suitable for year round testing.

Approximately 20 male panelists were used as the test population. Panelist flex areas must be free of any skin condition (eczema, dryness, irritation, cuts or abrasions). Anyone taking antihistamines, anti-inflammatory drugs (more than 8 per week) or topical, oral or injectable cortisone on a regular basis was excluded from the study. The panel was divided into two subgroups which are balanced for left handedness. Group I was assigned composition "A" for the left flex and "B" for the right flex. Group II reversed the order.

Following an evaluation, the panelist was instructed to moisten the left flex area. Sponge and test compositions when formulated as toilet bars were dampened with tap water (100 ppm calcium/magnesium ions). The sponge was then stroked over the test bar 10 times by the evaluator. The "dosed" sponge was placed in panelist's right hand. Panelist then washed his left flex area for exactly 60 seconds (approximately 120 strokes). Thereupon, the flex was rinsed and patted dry. This washing procedure was repeated on right arm with the appropriate composition. Washing by this procedure was repeated 3 times daily for 5 consecutive days or a total of 15 washes. Treatment times were scheduled 1.5 hours apart. Each test site was evaluated immediately prior to washing and 4 hours after the third daily wash.

One trained assessor evaluated test sites prior to each wash and 4 hours after third wash of each day for a total of 20 evaluations. The grading scale was as follows:
 0=no erythema
 0.5—barely perceptible erythema
 1—mild spotty erythema/no edema
 1.5—mild/moderate erythema/with or without edema
 2—moderate confluent erythema/with or without edema or vesiculation
 2.5—Moderate/deep erythema/edema/vesiculation
 3—Deep erythema/edema/vesiculation/weeping Each site was treated in the prescribed method until a grading of "2" or greater was attained or 15 washings had been completed. When a score of "2" or greater was attained the treatment was discontinued on that flex. The final score was then carried through for all remaining evaluations. The remaining flex was washed until either a grading of at least "2" or 15 treatments were attained, whichever was first. In the Examples of this specification, the final grading is the sum total of grade scores for 20 assessments per panelist averaged over the scores from all panelists. Thus, theoretically the average score could range from 0 to 60; the lower value indicating absolutely no skin irritation while the latter being severe. In practice, scores generally ranged from about 15 to 30.

The following examples will more fully illustrate the embodiments of this invention. All parts, percentages and proportions referred to herein and in the appended claims are by weight of the total composition unless otherwise stated.

EXAMPLE 1

Sodium isethionate was evaluated herein for its mildness properties in combating the harsh effects of soap on the skin. Two formulations were tested; one was a control composition of 82/18 soap (tallow: coconut), the other additionally containing 15% sodium isethionate. Eight percent aqueous solutions were prepared by warming the compositions to 40° C. and preparing blind labels for each sample. A Frosch-Kligman Soap Chamber Test was conducted according to the procedure outlined, vide supra. Results of these tests are listed as Mean Assessment and Preference Scores in Tables I and II, respectively.

TABLE I
Frosch-Kligman Test Results With Aqueous Soap Solutions and Sodium Isethionate

| | Mean Assessment Score | | | | | |
|---|---|---|---|---|---|---|
| | Erythema | | Scaling | | Fissuring | |
| Sodium Isethionate: | 0% | 15% | 0% | 15% | 0% | 15% |
| Day 5 | 0.88 | 0.58 | 0.94 | 0.64 | 0.61 | 0.41 |
| Day 8 | 0.23 | 0.17 | 0.56 | 0.36 | 0.14 | 0.06 |

TABLE II
Frosch-Kligman Test Results With Aqueous Soap Solutions and Sodium Isethionate

| | Mean Preference Score | | | | | |
|---|---|---|---|---|---|---|
| | Erythema | | Scaling | | Fissuring | |
| Sodium Isethionate: | 0% | 15% | 0% | 15% | 0% | 15% |
| Day 5 | 3.79 | 2.47 | 4.12 | 2.95 | 3.91 | 2.29 |
| Day 8 | 3.77 | 3.00 | 4.23 | 2.68 | 4.03 | 2.18 |

Values shown in Tables I and II were statistically significant at the 90% confidence level except for the fissuring assessment score. These tests were, because of necessity, performed during summer months when skin response to the Frosch-Kligman procedure is poorest. Response during the winter months usually provide scores approximately 2 to 7 times greater. Accordingly, the differences illustrated by Tables I and II between sodium isethionate containing soap compositions and those without are minimum values. They would be expected to be much greater under a more taxing winter environment.

Erythema assessment scores from Table I demonstrate that an 82/18 soap with 15% sodium isethionate is significantly milder on Day 5 than a control without isethionate. Scaling was also noticeably less using the 15% isethionate soap composition. Although fissuring assessment scores were not statistically different, fissuring preference scores did differentiate 15% isethionate as providing a statistically measurable improvement in this skin condition. Levels of 5 and 10% sodium isethionate were also evaluated but not recorded in the Tables. Increased improvement in erythema, scaling and fissuring for both assessment and preference scores were noted as the level of isethionate rose.

EXAMPLE 2

Illustrations of personal washing compositions in the form of toilet bars are provided below.

These compositions also illustrate the presence of sodium acyl isethionate as a further detergent component, albeit minor, in the soap/sodium isethionate compositions of this invention.

TABLE III
Toilet Bar Formulations Containing Soap/Acyl Isethionate/Sodium Isethionate

| Components | Sample 1 (Wt. %) | Sample 2 (Wt. %) | Sample 3 (Wt. %) | Sample 4 (Wt. %) |
|---|---|---|---|---|
| Sodium Soap (82/18) | 46.53 | 54.27 | — | — |
| Sodium Soap (60/40) | — | — | 62.9 | — |
| Potassium Soap (60/40) | — | — | 15.7 | — |
| Sodium Soap (45/55) | — | — | — | 79.5 |
| Sodium acyl isethionate | 19.94 | 23.26 | — | — |
| Sodium isethionate | 10.00 | 2.14 | — | — |
| Coconut fatty acid | 1.21 | 1.41 | — | — |
| Tallow/Coconut Fatty Acid (80/20) | — | — | — | 7.4 |
| Stearic Acid | 6.40 | 7.47 | — | — |
| Sodium chloride | 0.40 | 0.46 | 1.0 | 1.4 |
| Water | 14.00 | 9.00 | 18.7 | 9.2 |
| Miscellaneous (Perfume, colorants, preservatives) | 1.52 | 1.99 | 1.0 | 2.1 |

Sample compositions 3 and 4 are well known toilet soaps; they served as control bars. Ratios associated with the sodium and potassium soaps refer to their relative content of tallow to coconut fatty acid residues.

EXAMPLE 3

Frosch-Kligman Soap Chamber Tests were conducted on Samples 1–4 of Example 2. The procedure was as outlined previously with the exception that 42 qualified panelists participated in the experiments and each was assigned one of 20 randomized patch sequences. Also, unlike the solutions of Example 1, toilet bars were used in this Example and grated into 40° C. water to provide 8% soap solutions (w/v). Results of the chamber tests are recorded in Tables IV, V and VI.

TABLE IV
Mean Erythema Scoring

| | Sample | | | |
|---|---|---|---|---|
| | 1 | 2 | 3 | 4 |
| | Preference | | | |
| Day 5 | 2.202 | 2.786 | 3.012 | 4.678 |
| Day 8 | 2.202 | 2.917 | 3.345 | 4.631 |
| | Assessment | | | |
| Day 5 | 0.849 | 1.079 | 1.039 | 2.341 |
| Day 8 | 0.413 | 0.794 | 1.071 | 1.659 |

TABLE V
Mean Scaling Score

| | Sample | | | |
|---|---|---|---|---|
| | 1 | 2 | 3 | 4 |
| | Preference | | | |
| Day 8 | 2.232 | 2.826 | 3.558 | 4.837 |
| | Assessment | | | |
| Day 8 | 0.833 | 1.159 | 1.452 | 2.008 |

TABLE VI
Mean Fissuring Score

| | Sample | | | |
|---|---|---|---|---|
| | 1 | 2 | 3 | 4 |
| | Preference | | | |
| Day 8 | 2.321 | 3.083 | 3.500 | 4.619 |
| | Assessment | | | |
| Day 8 | 0.532 | 0.770 | 0.928 | 1.682 |

On Day 5 and 8, erythema assessment and preference scores for Sample 1 containing 10% sodium isethionate was significantly better than the control soap bar Samples 3 and 4. Sample 2 with 2.14% sodium isethionate was also found milder than either soap control Samples 3 and 4.

Scoring for scaling on Day 5, when the patch was freshly removed, was without statistical significance. The reason for insignificance was that the area was still moist due to occlusion. On Day 8, the scoring pattern was identical with the fissuring and erythema scoring pattern. Thus, the order of decreasing mildness was: Sample 1, 2, 3 and then 4. Sodium isethionate present at 10% inhibited scaling more than when present at 2%. Compositions lacking isethionate performed poorest in this area of skin protection.

Fissure scoring on Day 5 was statistically equivalent among all Samples. On Day 8, fissuring scores revealed skin damage with increasing severity in the order Sample 1, 2, 3 and then 4. The pattern for fissuring was, therefore, identical with that for erythema and scaling. These results all indicate that sodium isethionate ameliorates skin damage causes by soap. Greater amounts of this skin mildness factor provide greater benefit.

The aforementioned Frosch-Kligman Test was conducted in the winter months. Score values for this evaluation were considerably higher as a group than that obtained with Samples of Example 1 taken during summer months.

EXAMPLE 4

This Example illustrates the skin damage control effect of sodium isethionate as evaluated by the Flex Wash Procedure. Two toilets bars were prepared. Bar A was essentially composed of a 60/40 (tallow/coconut) sodium fatty acid soap base and served as the control sample. Bar B was identical to the control except that it contained 10% sodium isethionate, the ratio of sodium isethionate to soap being 0.11.

TABLE VII

Flex Wash Test of Sodium Isethionate

| Bar | Flex Wash Score |
|---|---|
| A (Control) | 30.1 |
| B | 26.2 |

In the experiment, 17 panelists, divided into two groups, participated in the study. Subjects of one group were asked to apply Bar B to their left arm and Bar A to their right arm. The other group did the opposite. Four daily readings for 5 consecutive days were obtained. The fourth reading each day was made 4 to 5 hours after the last treatment. This was when the peak of the erythema occurred. Erythema was judged according to a 7 point scale that ranged from 0 (no erythema) to 3 (deep erythema), vide supra. Treatment was discontinued on an arm if a reading of 2 or more was obtained on that arm. Treatment continued on the other arm.

A statistical analysis of the above experiment indicated that Bar B was significantly milder to the skin than the control without sodium isethionate. Statistical analysis gave an alpha level value of 0.0349 between the two soaps demonstrating the signficance of the flex values. Further, control Bar A registered a 2 on the erythema scale before the other arm, in 7 of the 17 panelists. There were no instances where Bar B registered a 2 before A. This is significant at the alpha level 0.0078, using the Sign Test.

EXAMPLE 5

Sodium isethionate effects upon the skin were here evaluated using the Guinea Pig Immersion Test. Two aqueous solutions were prepared (control solution C contained 0.75% soap, 0.75% sodium acyl isethionate, 0.4% stearic acid and 0.07% sodium isethionate). Composition D was an aqueous solution identical to C except that the level of sodium isethionate was raised from 0.07% to 0.27%. The ratio of sodium isethionate to soap in solution C and D was 0.093 and 0.36, respectively. Immersion test results are outlined in the following Table.

TABLE VIII

Guinea Pig Immersion Test With Sodium Isethionate

| | Relative Response Scores | | |
|---|---|---|---|
| Composition | Erythema | Flaking | Roughness |
| C (Control) | 1.00 ± .19 | 0.68 ± .10 | 0.86 ± .20 |
| D | 0.67 | 0.40 | 0.47 |

Table VIII above demonstrates that as the level of sodium isethionate is raised relative response scores for all categories of skin damage (erythema, flaking, roughness) are lowered. The improvement was statistically significant.

EXAMPLE 6

The following Example illustrates compositions of this invention wherein soap and sodium isethionate are combined with a second detergent active.

TABLE IX

Soap/Sodium Isethionate Formulations

| Component | Sample (% Weight) | | | | | | |
|---|---|---|---|---|---|---|---|
| | 1 | 2 | 3 | 4 | 5 | 6 | 7 |
| Sodium fatty acid soap | 50 | 50 | 80 | 70 | 70 | 70 | 70 |
| Sodium isethionate | 50 | 30 | 10 | 10 | 10 | 10 | 10 |
| Sodium acyl isethionate | | 20 | | | | | |
| Dodecyl benzene sulfonate | | | | 20 | | | |
| $C_6$—$C_{14}$ dialkyl sulphosuccinate ester | | | | | 20 | | |
| $C_{12}$—$C_{18}$ alkyl sulfate | | | | | | 20 | |
| $C_{12}$—$C_{18}$ alkyl ether sulfate | | | | | | | 20 |

EXAMPLE 7

The following illustrates soap formulations containing various alkyl sodium isethionates.

TABLE X

Soap/Sodium Alkyl Isethionate Compositions

| Component | Sample (% Weight) | | | | | | | |
|---|---|---|---|---|---|---|---|---|
| | 1 | 2 | 3 | 4 | 5 | 6 | 7 | 8 |
| Sodium fatty acid soap | 60 | 60 | 50 | 50 | 60 | 70 | 60 | 70 |
| Sodium 2-methyl isethionate | 40 | | 5 | | 10 | 2 | 20 | 10 |
| Sodium 2-hexyl isethionate | | 40 | | 5 | | | | |
| Sodium acyl isethionate | | | 45 | 45 | 30 | 28 | | |
| $C_6$—$C_{14}$ dialkyl sulfosuccinate ester | | | | | | | 20 | 20 |

The foregoing description and Examples illustrate selected embodiments of the present invention and in light thereof various modifications will be suggested to one skilled in the art, all of which are within the spirit and purview of this invention.

What is claimed is:

1. A toilet bar composition consisting essentially of:
   (a) from 30 to 70% alkali metal fatty acid soap;
   (b) from about 2 to 15% of sodium isethionate;
   (c) from 1% to 15% $C_{12}$–$C_{18}$ free fatty acid; and
   (d) from 5% to 45% sodium $C_8$–$C_{18}$ acyl isethionate, the amount of acyl isethionate being no greater than the amount of soap present.

2. A composition according to claim 1 wherein the amount of sodium isethionate ranges from 4% to 15% by weight of the total composition.

3. A composition according to claim 1 wherein the free fatty acid is present from 4 to 10%.

4. A composition according to claim 1 wherein the free fatty acid is present from 5% to 9%.

5. A composition according to claim 1 wherein the free fatty acid is present from 6% to 8%.

6. A composition according to claim 1 wherein the free fatty acid is stearic acid.

7. A composition according to claim 1 further comprising adjunct toilet bar ingredients selected from the group consisting of perfumes, colorants, preservatives, electrolyte salts, pigments, water and mixtures thereof.

* * * * *